United States Patent [19]

Goode

[11] 4,402,314

[45] Sep. 6, 1983

[54] SURGICAL NASAL SEPTUM SPLINT

[76] Inventor: Richard L. Goode, 1583 Arbor Ave., Los Altos, Calif. 94022

[21] Appl. No.: 294,312

[22] Filed: Aug. 19, 1981

[51] Int. Cl.$^3$ ............................ A61F 5/04; A61F 5/08
[52] U.S. Cl. ................................ 128/76 C; 128/87 R; 128/342; 128/346
[58] Field of Search ................... 128/346, 76 C, 87 R, 128/1 R, 201.18, 206.11, 132 R, 342, 1.3, 89 R, 82; 24/201 B

[56] References Cited

U.S. PATENT DOCUMENTS

| | | | |
|---|---|---|---|
| 2,202,748 | 5/1940 | Solo | 128/342 X |
| 3,924,631 | 12/1975 | Mancusi, Jr. | 128/346 |
| 3,935,859 | 2/1976 | Doyle | 128/342 X |
| 4,033,342 | 7/1977 | Lake | 128/346 X |
| 4,255,837 | 3/1981 | Holtz | 24/201 B X |
| 4,336,806 | 6/1982 | Eldridge, Jr. | 24/201 B X |

Primary Examiner—Richard J. Apley
Assistant Examiner—Michelle N. Lester
Attorney, Agent, or Firm—Arthur G. Yeager

[57] ABSTRACT

A surgical nasal septum splint comprising a pair of members, each of which having a thin, flat body with a posterior end adapted to be inserted into the nasal passage and to be positionable interiorly thereof and with an anterior end adapted to be positionable adjacent the nasal columella, said body carrying a plurality of spaced magnets, the magnets adjacent the anterior end having a different polarity from the magnets adjacent the posterior end of each body, and the correspondingly positioned magnets in said pair of members being of opposite polarity so as to be attracted to each other when the members are in place on opposite sides of the nasal septum.

19 Claims, 5 Drawing Figures

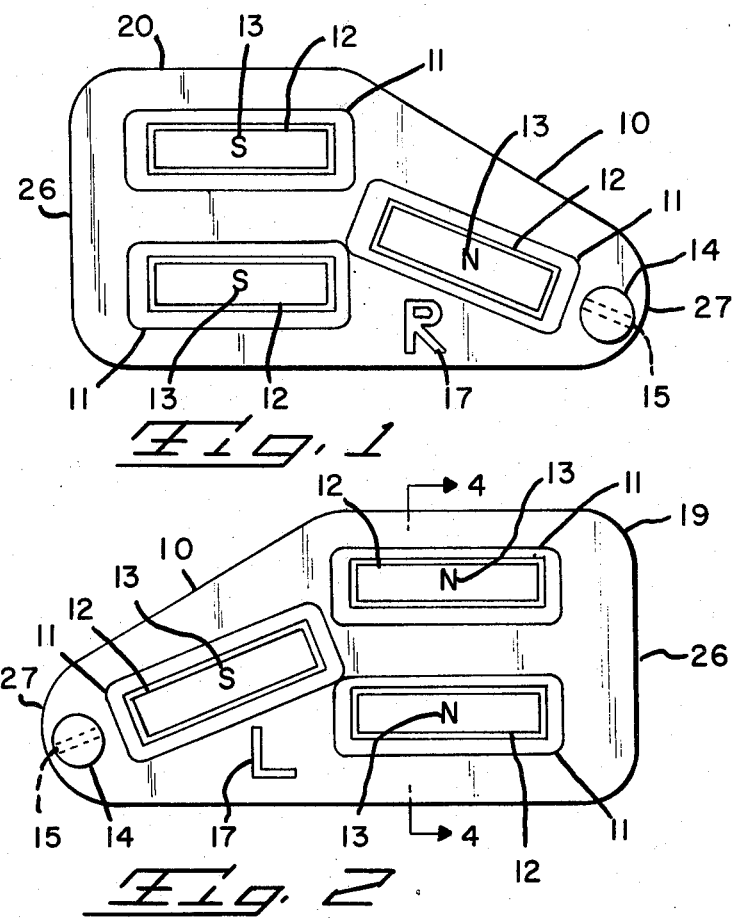
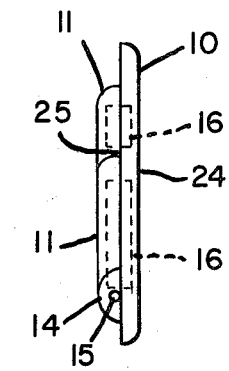
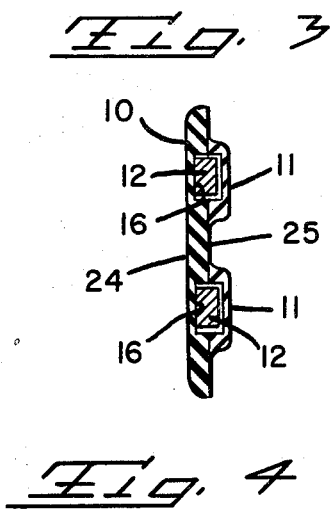
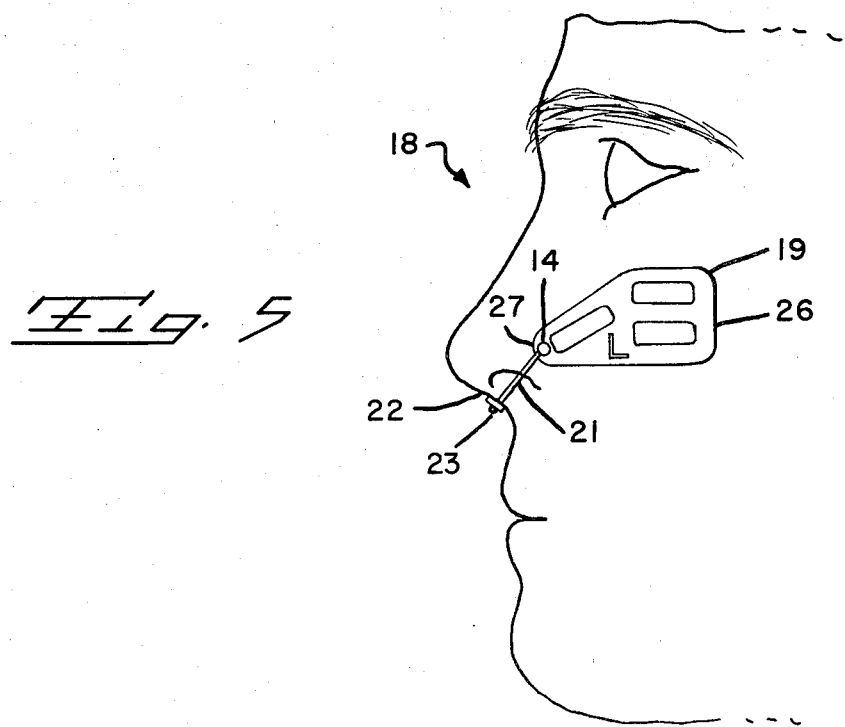

SURGICAL NASAL SEPTUM SPLINT

BACKGROUND OF THE INVENTION

Nasal surgery to correct a deviated or broken septum usually requires the use of some type of splint or packing to hold broken portions of the septum in place during the healing process, which may be a period of several weeks. Packing produces abnormal restrictions in the nasal passages which interferes with breathing through the nose to such an extent that it may be necessary to breathe through the mouth. This becomes uncomfortable after sustained periods of time and causes drying of the mouth. Splints which have been designed and used in the past have also been uncomfortable and generally are of such a size that they interfere with normal breathing. Thus, an improved nasal splint has been a much needed article for many years.

It is an object of this invention to provide a small nasal splint which is easy to apply and which does not seriously obstruct nasal breathing. Other objects will appear in a more detailed description of this invention which follows.

BRIEF SUMMARY OF THE INVENTION

This invention provides a surgical nasal septum splint comprising a pair of members, each member comprising a thin, flat body containing means which is magnetically attracted to the other member of said pair with sufficient strength to maintain both of said members immobile pressing against opposite sides of the nasal septum. In a special embodiment the body has a posterior end adapted to be inserted in the nasal passage and positionable interiorly thereof and an anterior end adapted to be positioned adjacent the nasal columella, said body carrying a plurality of spaced magnets, said magnets adjacent said anterior ends of said pair of members having a different polarity from said magnets adjacent said posterior ends of said pair of members, the correspondingly positioned magnets in said pair of members being of opposite polarity so as to be attracted to each other. The splint preferably includes means to attach the anterior end of each member to each other outwardly of the nasal columella. In a preferred embodiment of this invention the body member is made of silicone elastomer and the magnets are made of an alloy of cobalt and a rare earth and in the shape of a thin, elongated rectangular article.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken into connection with the accompanying drawing in which:

FIG. 1 is a top plan view of the right hand member of the splint in accord with this invention;

FIG. 2 is a top plan view of the left hand member of the splint in accord with this invention;

FIG. 3 is an end elevational view of the member in FIG. 1;

FIG. 4 is a cross sectional view along line 4—4 of FIG. 2; and

FIG. 5 is a schematic illustration of the splint of this invention in place in the nasal passage of the patient.

DETAILED DESCRIPTION OF THE INVENTION

In the attached drawing there are shown the details of the splint of this invention and how it is used to hold portions of the septum in place during the healing process.

The splint in accord with this invention comprises two members that preferably are mirror images of each other, left hand member 19 and and right hand 20. Each member comprises a thin flat body 10 having an inner surface 24 which is a flat continuous planar surface and an outer surface 25 into which have been molded a plurality of recesses 16 to receive a corresponding plurality of magnets 12. Each magnet 12 is covered with a cap 11 which is sealed completely around its perimeter to body 10 to encapsulate each magnet 12. Body 10 and caps 11 are made of a firm, resilent material which has no irritating effect upon the tissues of the nasal passages. A particularly preferred material for this purpose is a silicone elastomer. Such a material is well known and is available commercially from any of several plastic manufacturers. The sealing of cap 11 to body 10 is preferably accomplished by the use of a suitable adhesive, such as a solution of silicone in a solvent. These adhesives are also well known and available commercially.

Magnets 12 are preferably thin, light in weight, and sufficiently strong to be attracted to a corresponding magnet on the other side of the septum. It has been found that a suitable material for such magnets is an alloy of a rare earth and cobalt having a coercive force of at least 8,000 oersteds. Such magnets are available commercially from several sources. Preferably these magnets are employed in the form of a long, thin, flat rectangle that can provide some support to the septum over a substantial area when a plurality of magnets is used. A typical magnet employed in the process of this invention may be one having a rectangular cross section of approximately 1/16 inch by $\frac{1}{8}$ inch and is about $\frac{1}{2}$ inch long.

A plurality of magnets 12 should be used in the splint of the invention to provide the force necessary to hold the septum in place. This may be accomplished by any of several alternative overall designs of the splint. In the preferred embodiment each member 19 and 20 of the splint has a broad posterior end 26 and a narrow anterior end 27. Posterior end 26 is positioned interiorly of the nasal passage, and anterior end 27 is positioned near the nostril adjacent the nasal columella 22 as seen in FIG. 5. The breadth of posterior end 6 is limited by the size of the nostril but is broad enough to cover a substantial area of the septum on the inside of the nasal passage. A preferred placement and arrangement for the magnets 12 in each of members 19 and 20 is to provide at least two vertically spaced, horizontally positioned, parallel magnets near posterior end 26. One magnet 12 is positioned near anterior end 27 and is angularly disposed with respect to the parallel magnets in posterior end 26. By employing magnets of the size mentioned above in a normal splint it has been found that three of such magnets positioned as shown in the drawings are sufficient in each splint member to provide more than adequate support for the septum.

The selection of polarity of each magnet of members 19 and 20 is preferably made to permit ready introduction of each member into the nasal passage, and to provide a firm positioning once members 19 and 20 are in place. It is, of course, necessary that each pair of cooperating magnets, i.e. a magnet in each of members 19 and 20 in a corresponding location must be of opposite polarity in order to be attracted to each other and thereby provide the force necessary to hold the two halves of the splint in a substantially fixed position. This purpose can be accomplished merely by making all of the magnets in one member have north polarity and all of the magnets in the other member have a south polarity. While such an arrangement is operable, it is not preferred because when the second member, 19 or 20, is introduced into the nasal passage after the first member has previously been positioned in the nasal passage, the magnetic attraction between members 19 and 20 functions as soon as the second member is inserted into the nostril which makes it difficult to adjust the second member into place. In order to avoid this premature magnetic attraction and to permit easy adjustment of the two members 19 and 20, the polarity of the magnet in anterior end 27 is preferably made opposite from that of magnets in posterior end 26. Correspondingly positioned magnets in each of two members 19 and 20, however, must be of opposite polarity to maintain a strong magnetic attraction between members 19 and 20 when the splint halves are in the opposing face-to-face relationship. The arrangement of polarities 13 as shown in FIGS. 1 and 2 will provide the ease of positioning as mentioned above.

As an illustration of the advantage of properly arranging the polarities of magnets 12 assume that right hand member 20 has been inserted into the right nasal passage of patient 18 and that left hand member 19 is about to be inserted into the left hand nasal passage. As posterior end 26 of member 19 is inserted into the left nostril, the two magnets 12 having a north polarity will be passing on the opposite side of the septum to single magnet 12 having a north polarity in anterior end 27 of right hand member 20. Since these magnets are of the same polarity there will be a repulsive force between these magnets permitting left hand member 19 to be easily inserted farther into the left nasal passage of patient 18. When left hand member 19 is inserted far enough into the nasal passage to approach alignment with member 20, the corresponding magnets will be attracted to each other because of their opposite polarity. This attraction assists in automatically aligning members 19 and 20 so that each pair of cooperating magnets are directly opposite each other. To restrain members 19 and 20 from moving inwardly after insertion into the nasal passages, a means is provided to attach anterior ends 27 of each member 19 and 20 to each other. Such restraint is necessary to eliminate the danger that either of members 19 and 20 might move deeper into the breathing passages of patient 18 as the result of sudden movements of the head or large intakes of air. In accord with the invention the means shown include a thickened bead 14 at anterior end 27 of each of members 19 and 20 with a hole 15 through bead 14 to permit a filament, thread, suture, or the like, 21 to be inserted therethrough and tied into a knot 23 outside the nasal columella 22 of patient 18. It is to be understood that a releasable type of knot could be provided, if desired.

There is also shown in these drawings an identifying letter 17 to indicate which of the two members 19 and 20 is to be inserted in the left nasal passage and which in the right nasal passage of the patient. This is merely a designation integrally molded on the surface of base sheet 10 for the convenience of the doctor.

The scope of this invention is intended to cover nasal septum splints which are held in place by magnetic attraction regardless of the shape, size, or design of the splint. Shapes other than the rectangular one shown in the drawings will be desirable in certain instances. It will, of course, be necessary to provide splints of various sizes to accommodate the nasal septums of any from infants to full grown adults. The number of magnets included in the splint may be whatever necessary to hold the splint in place. It is also feasible to employ magnetic material dispersed throughout the splint body rather than to embed one or more magnets in each splint half.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A surgical nasal splint comprising a pair of mirror image members adapted to be placed in the nasal passage with each member of said pair aligned on opposite sides of the nasal septum, each said member including a thin flat body, permanent magnet means attached to each said body for magnetically attracting said pair of members toward each other, said means having a mutually attractive force for maintaining said members immobile while pressing against each other from opposite sides of the nasal septum.

2. The splint of claim 1 wherein said means includes a magnet embedded in said body.

3. The splint of claim 1 wherein said means comprises a magnetic substance distributed throughout said body.

4. The splint of claim 1 wherein said body is a silicone elastomer.

5. A surgical nasal septum splint comprising a pair of members, each member comprising a thin flat body having a posterior end adapted to be inserted in the nasal passage and positionable interiorly thereof and an anterior end adapted to be positioned adjacent the nasal columella, said body carrying a plurality of spaced magnets, said magnets adjacent said anterior ends of said pair of members having a different polarity from said magnets adjacent said posterior ends of said pair of members, the correspondingly positioned magnets in said pair of members being of opposite polarity so as to be attracted to each other.

6. The splint of claim 5 wherein said members are made of a silicone elastomer.

7. The splint of claim 5 wherein said magnets are made of an alloy of cobalt and a rare earth.

8. The splint of claim 5 which additionally includes means to attach said anterior ends of each of said pair of members to each other outside of the nasal columella.

9. The splint of claim 5 wherein each of said pair of members includes a magnet in said posterior end and a magnet in said anterior end.

10. The splint of claim 9 wherein each said posterior end contains two elongated, rectangular magnets positioned generally horizontally and spaced apart vertically from each other.

11. The splint of claim 10 wherein said magnet in said anterior end is angularly disposed with respect to said magnets in said posterior end.

12. The splint of claim 5 wherein each said body has an inner surface which is substantially planar and is adapted to be placed against said septum.

13. The splint of claim 8 wherein said means to attach said anterior ends to each other comprises a filament attached to each of said anterior ends and capable of being tied to each other outside said nasal columella.

14. The splint of claim 5 wherein each of said members comprises a substantially flat planar base sheet with a plurality of shallow recesses with one of said magnets in each recess, and a cap fitting over each magnet and sealed to said base sheet so as to provide a plurality of separate, encapsulated magnets.

15. The splint of claim 5 wherein each of said magnets exhibits a coercive force of at least 8000 oersteds.

16. The splint of claim 5 wherein said anterior end is generally triangular in shape and said posterior end is generally square, all corners of said body being rounded.

17. The splint of claim 16 wherein each of said members contains three thin, elongated, and generally rectangular magnets, two of said magnets being vertically spaced apart and positioned in said posterior end in a generally horizontal orientation, parallel to each other, and one of said magnets being positioned in said anterior end angularly disposed downwardly from said horizontal magnets in said posterior end to said anterior end.

18. The splint of claim 5 which includes on each of said members at said anterior end a thickened portion adapted to receive a filament therethrough.

19. The splint of claim 17 wherein said magnets on said posterior end on one of said members are of the same polarity and are opposite in polarity to said magnets on said posterior end on the other of said members.

* * * * *